(12) United States Patent
Shashiprabha et al.

(10) Patent No.: US 8,410,268 B2
(45) Date of Patent: Apr. 2, 2013

(54) PROCESS FOR THE PREPARATION OF ZIPRASIDONE

(75) Inventors: Shashiprabha, Bangalore (IN); Kanakamajalu Shridhara, Bangalore (IN); Debkiron Mukherjee, Bangalore (IN); Padmashree Badraje, Bangalore (IN); K Sundarraja Rao, Bangalore (IN); Kuppuswamy Nagarajan, Bangalore (IN)

(73) Assignee: Alkem Laboratories Limited, Mumbai (IN)

( * ) Notice: Subject to any disclaimer, the term of this patent is extended or adjusted under 35 U.S.C. 154(b) by 161 days.

(21) Appl. No.: 12/921,566

(22) PCT Filed: Mar. 9, 2009

(86) PCT No.: PCT/IN2009/000164
§ 371 (c)(1),
(2), (4) Date: Sep. 8, 2010

(87) PCT Pub. No.: WO2009/116085
PCT Pub. Date: Sep. 24, 2009

(65) Prior Publication Data
US 2011/0003995 A1    Jan. 6, 2011

(30) Foreign Application Priority Data
Mar. 11, 2008    (IN) .......................... 499/MUM/2008

(51) Int. Cl.
*C07D 417/12* (2006.01)
(52) U.S. Cl. .................... 544/368; 514/254.04
(58) Field of Classification Search ........................ None
See application file for complete search history.

(56) References Cited

U.S. PATENT DOCUMENTS

| | | | | |
|---|---|---|---|---|
| 4,831,031 A | * | 5/1989 | Lowe et al. | 514/254.02 |
| 5,206,366 A | * | 4/1993 | Bowles | 544/368 |
| 5,312,925 A | * | 5/1994 | Allen et al. | 544/368 |
| 5,338,846 A | * | 8/1994 | Busch et al. | 544/368 |
| 6,150,366 A | * | 11/2000 | Arenson et al. | 514/254.04 |

* cited by examiner

*Primary Examiner* — Emily Bernhardt
(74) *Attorney, Agent, or Firm* — George W. Moxon, II; Brian P. Harrod

(57) ABSTRACT

The present invention relates to a process for preparing Ziprasidone of formula I,

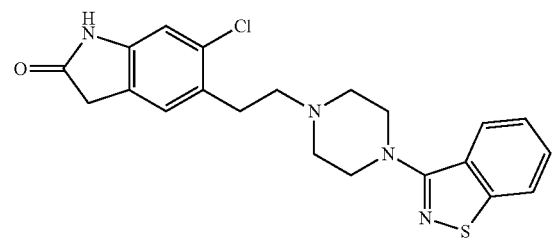

(I)

or a pharmaceutically acceptable salt or a solvate or a hydrate thereof;
comprising the steps of reacting 1-(1,2-benzisothiazol-3-yl) piperazine of formula II or its salt:

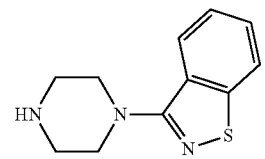

(II)

with 5-(2-haloethyl)-6-chloro-oxindole of formula III:

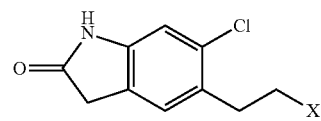

(III)

wherein X is leaving groups like fluoro, chloro, bromo, iodo or sulphonyl;
in the presence of a dispersing agent and a base in a solvent to form ziprasidone of formula I; and optionally converting the ziprasidone formed into a pharmaceutically acceptable acid addition salts of ziprasidone; or a solvate or a hydrate thereof.

9 Claims, No Drawings

PROCESS FOR THE PREPARATION OF ZIPRASIDONE

FIELD OF THE INVENTION

The present invention relates to an improved process for the preparation of ziprasidone or pharmaceutically acceptable salts thereof.

BACKGROUND OF THE INVENTION

Ziprasidone is an antipsychotic agent with the following chemical name: 5-[2-[4-(1,2-benzisothiazol-3-yl)-1-piperazinyl]ethyl]-6-chloro-1,3-dihydro-2H-indol-2-one of formula (I)

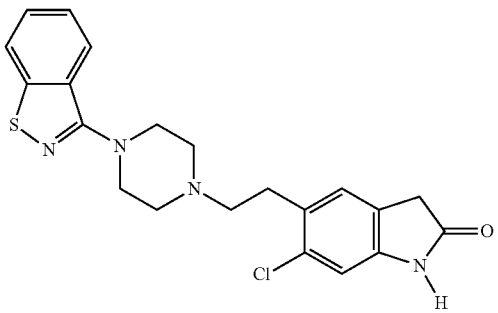

(I)

Ziprasidone is disclosed in U.S. Pat. Nos. 4,831,031 and 5,312,925 (assigned to Pfizer). Ziprasidone inhibits synaptic reuptake of serotonin and norepinephrine. No appreciable affinity was exhibited for other receptor/binding sites tested, including the cholinergic muscarinic receptor. The mechanism of action of ziprasidone, as with other drugs having efficacy in schizophrenia, is unknown. However, it has been proposed that this drug's efficacy in schizophrenia is mediated through a combination of dopamine type 2 (D 2) and serotonin type 2 (5HT 2) antagonism. Ziprasidone's antagonism of histamine H receptors may explain the somnolence observed with this drug.

U.S. Pat. No. 5,312,925 (Pfizer Inc.) describes a process for the synthesis of monohydrate of 5-(2-(4-(1,2-benzisothiazol-3-yl)piperazinyl)ethyl)-6-chloro-1,3-dihydro-2H-indol-2-one hydrochloride and its characterization based on IR, XRD and moisture content. The '925 patent also discloses that the hemihydrate may be obtained by the process described in Example 16 of U.S. Pat. No. 4,831,031 and its characterization by IR, XRD and moisture content. It also discloses the IR, XRD and moisture content of anhydrous Ziprasidone hydrochloride. According to the invention in the '925 patent, Ziprasidone of water content of 3.97, 2.55 and 0.37% were used for the IR and XRD study of Ziprasidone hydrochloride monohydrate, hemihydrate and anhydrous. In this invention, the monohydrate of Ziprasidone hydrochloride was prepared by reacting anhydrous 5-(2-(4-(1,2-benzisothiazol-3-yl)piperazinyl)ethyl)-6-chloro-1,3-dihydro-2H-indol-2-one with aqueous hydrochloric acid. The temperature range of the reaction was maintained between 60 to 65° C. and aqueous hydrochloride used for salt formation was around 0.7 M. Depending on the reaction temperature and other conditions, the reaction times were set around 3 to 24 hours. The final product thus obtained was dried carefully in monitored conditions to make certain that water content was from about 3.8% to about 4.5% to obtain the stable monohydrate.

U.S. Pat. No. 6,150,366, discloses a manufacturing process of ziprasidone hydrochloride monohydrate, comprises: 1) dissolving, ziprasidone free base in a solvent comprising THF and water, in a volume ratio of about 22-35 unit volumes of THF to about 1.5-8 volumes of water; 2) heating the solution resulting from step (1); 3) adding HCl to the solution resulting from step (2); and 4) cooling the solution resulting from step (3) and crystals collected by filtration and drying.

U.S. Pat. No. 5,206,366 and U.S. Pat. No. 5,338,846 describe a process for preparing ziprasidone by reacting 1-(1, 2-benzisothiazol-3-yl) piperazine with 5-(2-chloroethyl)-6-chloro-oxindole in water with a neutralizing agent such as sodium carbonate under reflux.

J. Med. Chem. 1996, 39, 143-148 discloses preparation of ziprasidone by reacting 1-(1,2-benzisothiazol-3-yl)piperazine with 5-(2-bromoethyl)-6-chloro-oxindole in isoamyl alcohol solvent in the presence of sodium carbonate.

Some salts of ziprasidone, and in particular, its hydrochloride salt is a potent commercial antipsychotic agent useful in the treatment of various disorders, including schizophrenia and anxiety diseases. Ziprasidone hydrochloride is currently marketed under the proprietary name of Geodon. Other salts of ziprasidone are also reported to be effective for the treatment of the same type of diseases.

Some of the processes described in the aforementioned patents necessitate the use of ion-exchange catalyst (i.e. sodium iodide) and/or phase transfer catalysts (for example tetra butyl ammonium bromide or tetra butyl phosphoriium bromide) in order for the coupling reaction producing ziprasidone to take place. For example, U.S. Pat. No. 4,831,031 indicates that arylpiperazinyl-ethyl (or butyl)-heterocydic compounds may be prepared by reacting piperazines of the formula II with compounds of the formula III as follows in [Scheme 1]:

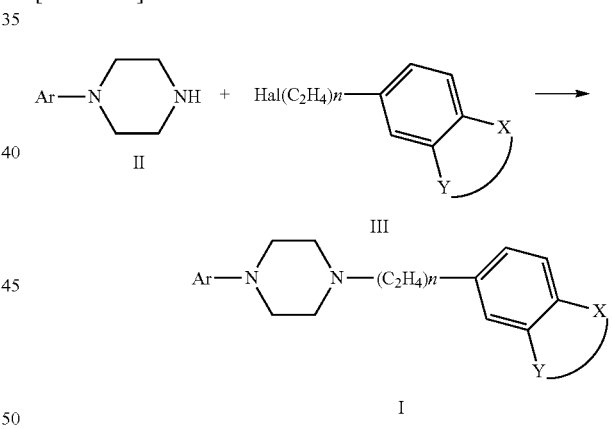

Wherein Hal is fluoro, chloro, bromo or iodo; and Ar, n, X and Y are as defined therein with reference to formula I. According to the '031 patent the coupling reaction is generally conducted in a polar solvent, such as a lower alcohol, dimethylformamide or methylisobutylketone, and in the presence of a weak base and that, preferably, the reaction is carried out in the presence of a catalytic amount of sodium iodide, hydrogen chloride and neutralizing agent such as sodium carbonate.

In some instances, the ziprasidone obtained was purified by column chromatography, thus making the process impractical for large-scale preparations. Another process uses potentially explosive gases such as hydrogen in the presence of catalysts, for example zinc, palladium on carbon, followed by acid treatment to carry out a reduction and cyclization of an intermediate, in order to obtain ziprasidone.

Despite various processes disclosed in the prior art for the preparation of ziprasidone and salts thereof, still there is a need for a good process for producing ziprasidone and pharmaceutically acceptable acid addition salts of ziprasidone thereof, in high purity. One of the major problems faced in the prior art is formation of sticky material and difficult stirrability of the reaction mass. This problem is especially acute in large scale manufacturing.

The present invention provides a process for the preparation of ziprasidone in high yields and purity, suitable for large-scale manufacturing, which helps to overcome some of the deficiencies of the prior art.

OBJECT OF THE INVENTION

It is an object of the present invention to provide an improved process for the preparation of ziprasidone of formula I or a pharmaceutically acceptable salt or a solvate or a hydrate thereof.

It is further object of the present invention to provide a process for the preparation of ziprasidone in high yields and purity, suitable for large-scale manufacturing, which helps to overcome some of the deficiencies of the prior art.

At least one of the preceding objects is met, in whole or in part, by the improved process of the invention, for preparing ziprasidone, or a pharmaceutically acceptable salt or a solvate or a hydrate thereof, by reacting 1-(1,2-benzisothiazol-3-yl) piperazine or its salt with 5-(2-haloethyl)-6-chloro-oxindole in the presence of dispersing agent and a base in a solvent.

SUMMARY OF THE INVENTION

According to first aspect of the present invention is provided an improved process for the preparation of ziprasidone of formula I or a pharmaceutically acceptable salt or a solvate or a hydrate thereof.

According to another aspect of the present invention is provided an improved process for preparing ziprasidone of formula I, or a pharmaceutically acceptable salt or a solvate or a hydrate thereof, comprising the steps of reacting 1-(1,2-benzisothiazol-3-yl) piperazine of formula II or its salts with 5-(2-haloethyl)-6-chloro-oxindole of formula III in the presence of dispersing agent and a base in a solvent [Scheme 2]. This surprisingly enabled production of pharmaceutical grade ziprasidone in an efficient manner with a yield and purity higher than the prior art processes.

Scheme 2:

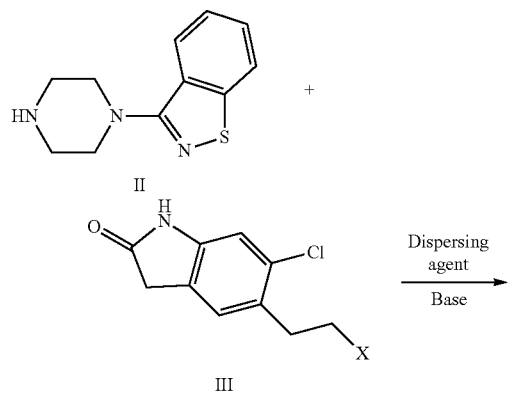

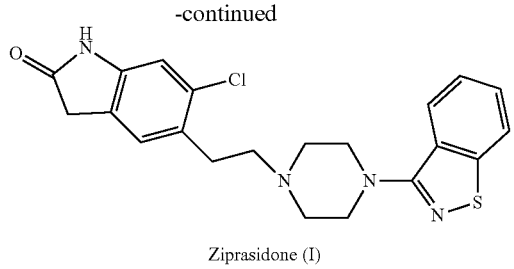

Ziprasidone (I)

The ziprasidone thus obtained is optionally converted into pharmaceutically acceptable acid addition salts or a solvate or a hydrate thereof.

The purpose of using dispersing agent in the reaction is to overcome the problem of sticky mass formation during the reaction. This sticky mass is not easily soluble in water and causes problems during the reaction and also in cleaning of the reactors. The sticky mass formation has its negative impact on the yields and also on product quality. Additionally the use of a dispersing agent results in pharmaceutical grade ziprasidone in an efficient manner with a yield and purity higher than the prior art processes.

The process of the present invention provides ziprasidone or a pharmaceutically acceptable salt or a solvate or a hydrate in a yield and purity higher than the prior art processes. It is preferred that the ziprasidone or the pharmaceutically acceptable salt thereof obtained by the present invention has a purity of at least 98%.

The invention may be summarized as given below:
A. A process for preparing ziprasidone of formula I,

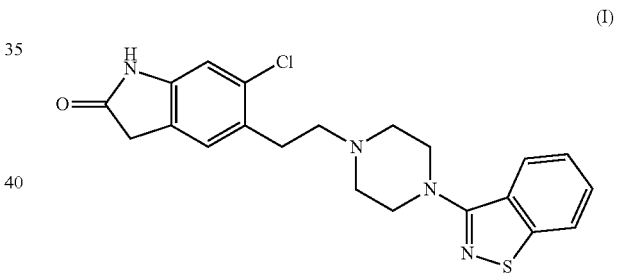

or a pharmaceutically acceptable salt or a solvate or a hydrate thereof;
comprising the steps of reacting 1-(1,2-benzisothiazol-3-yl) piperazine of formula II or its salt:

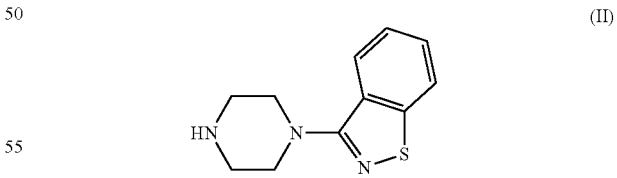

with 5-(2-haloethyl)-6-chloro-oxindole of formula III:

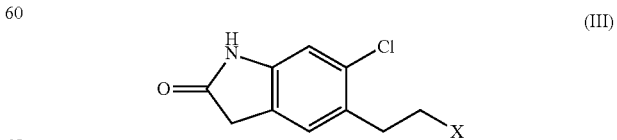

wherein X is leaving groups like fluoro, chloro, bromo, iodo or sulphonyl;

in the presence of a dispersing agent and a base in a solvent to form ziprasidone of formula I; and optionally converting the ziprasidone formed into a pharmaceutically acceptable acid addition salts of ziprasidone; or a solvate or a hydrate thereof.

B. Process as in step A above, wherein the dispersing agent is selected from modified sodium lignosulfonates such as BORRESPERSE™ Na, UFOXANE™ 3 and ULTRAZINE™ Na; Kraft sodium lignosulfonates such as REAX® 88B; naphthalene-formaldehyde condensates such as DISPERSOGEN® SI, MORWET® D-425 (naphthalene sulfonic acid formaldehyde) and GALORYL® DT 201 (naphthalene-sulfonic acid formaldehyde condensate); and the like or mixtures thereof.

C. Process as in step B above, wherein the dispersing agent is selected from naphthalene-formaldehyde condensates such as DISPERSOGEN® SI, MORWET® D-425 (naphthalene sulfonic acid formaldehyde) and GALORYL® DT 201 (naphthalenesulfonic acid formaldehyde condensate).

D. Process as in step C above, wherein the dispersing agent is MORWET® D-425 (naphthalene sulfonic acid formaldehyde).

E. Process as in step A above, wherein the base is selected from alkali metal salt, hydroxides, organic tertiary bases and the like or mixtures thereof.

F. Process as in step A above, wherein the base is selected from sodium carbonate or bicarbonate or mixtures thereof.

G. Process as in step A above, wherein the solvent is selected from the group comprising substituted, unsubstituted, cyclic, bicyclic, saturated, or unsaturated, straight or branched hydrocarbon but not limited to aliphatic or aromatic hydrocarbon, having $C_6$-$C_{10}$ atoms, water, alcohols, ketones, esters, ethers and chlorinated solvents, and the like or mixtures thereof.

H. Process as in step G above, wherein the solvent is selected from the group comprising toluene; esters such as ethyl acetate, propyl acetate, isopropyl acetate, butyl acetate and isobutyl acetate; water; alcohols such as methanol, ethanol and isopropanol; ketones such as acetone, methyl ethyl ketone, methyl isobutyl ketone and diethyl ketone; ethers such as tetrahydrofuran and dioxane; and chlorinated solvents such as methylene chloride, chloroform, carbontetrachloride and ethylene dichloride; and the like or mixtures thereof.

I. Process as in step H above, wherein the solvent is selected from the group comprising alcohols and water and the like or mixtures thereof.

J. Process as in step A above, wherein the prepared ziprasidone or pharmaceutically acceptable salt or a solvate or a hydrate thereof has a purity of at least 98%.

Further objects of the present invention together with additional features contributing thereto and advantages accruing there from will be apparent from the following description of preferred embodiments of the invention which are shown in the accompanying drawing figures wherein Scheme 1 is a schematic representation of an embodiment for prior art process for preparing arylpiperazinyl-ethyl (or butyl)-heterocyclic compounds, or a pharmaceutically acceptable salt, by reacting piperazines of the formula II with compounds of the formula III.

Scheme 2 is a schematic representation of an embodiment for process where a process for preparing ziprasidone of formula I, or a pharmaceutically acceptable salt or a solvate or a hydrate thereof, comprising the steps of reacting 1-(1,2-benzisothiazol-3-yl) piperazine/salt of formula II with 5-(2-haloethyl)-6-chloro-oxindole of formula III in the presence of dispersing agent and a base in a solvent.

DETAILED DESCRIPTION OF THE INVENTION

Before the present process and methods are described, it is to be understood that this invention is not limited to particular compounds, formulas or steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a compound" includes a plurality of such compounds and reference to "the step" includes reference to one or more step and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In accordance with the present embodiment, there is provided a process for the preparation of ziprasidone of formula I or a pharmaceutically acceptable salt or a solvate or a hydrate thereof.

In accordance with the present embodiment, there is provided a process for preparing ziprasidone of formula I, or a pharmaceutically acceptable salt or a solvate or a hydrate thereof, comprising the steps of reacting 1-(1,2-benzisothiazol-3-yl) piperazine of formula II or its salt with 5-(2-haloethyl)-6-chloro-oxindole of formula III in the presence of dispersing agent and a base in a solvent and optionally converting the ziprasidone formed into a pharmaceutically acceptable acid addition salts of ziprasidone; or a solvate or a hydrate thereof.

Though all pharmaceutically acceptable acid addition salts of formula II can be used, those salts in which the anion does not contribute significantly to toxicity of pharmacological activity of the organic cation, may be preferred. Examples of organic acids useful for making salt of compound of formula II are carboxylic acids such as maleic acid, acetic acid, tartaric acid, propionic acid, fumaric acid, isethionic, succinic acid, pamoic acid, cyclamic acid, pivalic acid, and the like; inorganic acids used are hydrohalide acids such as HCl, HBr, HI; sulfuric acid; phosphoric acid; and the like.

In the process of the present invention, the (1,2-benzisothiazol-3-yl) piperazine of formula II or its salt and 5-(2-haloethyl)-6-chloro-oxindole of formula III are used in the range of about 1:1 to about 10:1 of molar ratio to improve the yield of ziprasidone of formula I or a pharmaceutically acceptable salt or a solvate or a hydrate thereof.

The purpose of using dispersing agent in the reaction of the present invention is to overcome the problem of sticky mass that is formed during the reaction. This sticky mass is not easily soluble in water and causes problems in the reaction. Additionally the use of a dispersing agent results in pharmaceutical grade ziprasidone in an efficient manner with a yield and purity higher than the prior art processes. It enhances the mixing of the reaction mass and results in cleaner product.

The compounds that can be used as dispersing agent are for example, polymers of the arylsulphonate type, in particular the alkaline polynaphthalene sulphonates obtained by condensation of (alkyl) aryl sulphonate derivatives with formaldehyde, lignosulphonates (for example: sodium lignosulfonate and calcium lignosulphate), the polyphenol sulphonates, the salts of polyacrylic acids, the salts of lignosulphonic acids (for example: the sodium salt of polymerized lignosulphonic acids of the Kraft type), the salts of sulphonic phenol acids or sulphonic naphthalenes, the phosphoric esters of alcohols or of polyethoxylated phenols, the esters of fatty acids and of polyols, derivatives with a sulphates, sulphonates and phosphates function of the preceding compounds and the like or mixtures thereof.

Suitable for use as dispersants are, for example, modified sodium lignosulfonates, such as BORRESPERSE™ Na, UFOXANE™ 3A, and ULTRAZINE™ Na (manufactured by Borregard); Kraft sodium lignosulfonates, such as REAX® 88B (manufactured by Westvaco) or naphthaleneformaldehyde condensates, such as DISPERSOGEN® SI (manufactured by Clariant GmbH), MORWET® D-425 (manufactured by Witco Corporation) and GALORYL® DT 201 (manufactured by CFPI) and the like or mixtures thereof.

Preferred dispersants are sodium salts of alkylnaphthylsulfonic acid/formaldehyde condensates and sodium lignosulfonate which are commercially available, for example, under the trade names MORWET® D-425 and having the structure below:

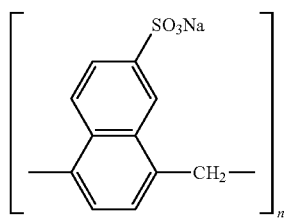

Wherein n ranges from 2 to 9,

Therefore, based on the object of discovering that the dispersing agents particularly MORWET® D-425 was found to give a product with lesser impurities, an efficient, high-yield and being a significantly cheaper raw material, it becomes an excellent source for the production of 5-[2-[4-(1,2-benzisothiazol-3-yl)-1-piperazinyl]ethyl]-6-chloro-1,3-dihydro-2H-indol-2-one. The invention accordingly provides, use of dispersing agent such as MORWET® D-425 in the process of the invention in presence of a base such as for example sodium hydroxide or sodium carbonate.

In accordance with the present invention, there is provided a reaction that is carried out in the presence of bases like alkali metal hydroxides, carbonates, bicarbonates and organic bases like tertiary amines like triethyl amine, benzisothiazolyl piperazine, pyridine etc. Alkali metal carbonates like sodium carbonate, potassium carbonate and more specifically sodium carbonate.

In accordance with the present invention, there is provided a process for preparing ziprasidone of formula I, wherein the solvent is selected from the group comprising alcohols, ketones, water, hydrocarbons, esters, ethers and chlorinated solvents, or mixtures thereof. The solvent may be selected from the group comprising alcohols, ketones, hydrocarbons, esters, ethers and chlorinated solvents, or mixtures thereof. The solvent used in the present invention is selected from the group consisting of substituted, unsubstituted, cyclic, bicyclic, saturated, or unsaturated, straight or branched hydrocarbon but not limited to aliphatic or aromatic hydrocarbon, having $C_6$-$C_{10}$ atoms, Suitable solvents are generally alcohols such as methanol, ethanol, isopropanol; ketones such as acetone, methyl ethyl ketone, methyl isobutyl ketone, diethyl ketone; hydrocarbon such as toluene, ester, ethyl acetate, propyl acetate, isopropyl acetate, butyl acetate, isobutyl acetate; water; ethers such as tetrahydrofuran, and dioxane; chlorinated solvents such as methylene chloride, chloroform, carbontetrachloride, ethylene dichloride and the like or mixtures thereof.

In an embodiment of the present invention, there is provided a process for preparation of ziprasidone by reacting piperazine benzisothiazole hydrochloride, 5-(2-chloroethyl)-6-chlorooxindole, sodium carbonate in which water is added 20 times based on oxindole weight and 1% of dispersing agent MORWET® D-425. All these reactants are charged in to the flask and refluxed under nitrogen, under stirring for 12-16 hr. After the completion of the reaction, the reaction mass is then cooled to room temperature and the resulting mass is filtered. It is slurried in water and then in IPA and isolated by filtration. The solid is dried at 95-100° C.

In another embodiment of the present invention, there is provided a process for preparation of ziprasidone by reacting piperazine benzisothiazole hydrochloride, 5-(2-chloroethyl)-6-chlorooxindole, and dispersing agent MORWET® D-425 and a base. All these reactants are charged in to the flask and refluxed under nitrogen, under stirring for 12-16 hr. After the completion of the reaction, the reaction mass is then cooled to room temperature and the resulting mass is filtered. It is slurried in IPA and then in water and isolated by filtration. The solid is dried at 95-100° C.

The ziprasidone prepared by the embodiments of the present process may be converted into a pharmaceutically acceptable acid addition salt; or a solvate or a hydrate thereof.

The process of the present invention provides ziprasidone or a pharmaceutically acceptable salt or a solvate or a hydrate in a yield and purity higher than the prior art process. It is preferred that the ziprasidone or the pharmaceutically acceptable salt thereof obtained by the present invention has a purity of at least 98%.

The following example illustrates the preparation of ziprasidone and is not to be construed as limiting the scope of the invention in any manner.

Example 1

2.2 moles of piperazine Benzisothiazole hydrochloride, 1 mol of 5-(2-chloroethyl)-6-chlorooxindole, 2.2 mol of Sodium hydroxide, water 20 times based on oxindole weight and 1% of dispersing agent MORWET® D-425. All the reactants are charged in to the flask and refluxed under nitrogen, under stirring for 12-16 hr. After the completion of the reaction, the reaction mass is cooled to room temperature and the resulting mass is filtered. It is slurried in IPA and then in water and isolated by filtration. The solid is dried at 95-100° C.

Yield: 90%; Purity: 98%

Example 2

1 mole of piperazine Benzisothiazole hydrochloride, 1 mole of 5-(2-chloroethyl)-6-chlorooxindole, 3.3 mole of Sodium carbonate, water 5.2 times based on oxindole weight and 1% of dispersing agent MORWET® D-425 are charged in to the flask and refluxed under nitrogen, under stirring for 12-16 hr. After the completion of the reaction, the reaction mass is cooled to room temperature and the resulting mass is filtered. It is slurried in water and then in IPA and isolated by filtration. The solid is dried at 95-100° C.

Yield: 90%; Purity: 100.30%

Example 3

2 moles of Piperazine Benzisothiazole hydrochloride, 1 mole of 5-(2-chloroethyl)-6-chlorooxindole in water (20 times based on benzisothiazole) and in the presence of dispersing agent. All the reactants are charged in to the flask and refluxed under nitrogen, under stirring for 12-16 hr. After the completion of the reaction, the reaction mass is cooled to room temperature and the resulting mass is filtered. It is slurried in IPA and then in water and isolated by filtration. The solid is dried at 95-100° C.

Yield: 90-92%, Purity 98% (min).

Example 4

2 moles of Piperazine Benzisothiazole, 1 mole of 5-(2-chloroethyl)-6-chlorooxindole in water (20 times based on benzisothiazole) and in the presence of dispersing agent. All the reactants are charged in to the flask and refluxed under nitrogen, under stirring for 12-16 hr. After the completion of the reaction, the reaction mass is cooled to room temperature and the resulting mass is filtered. It is slurried in water and then in IPA and isolated by filtration. The solid is dried at 95-100° C.

Yield: 92%, Purity 99% (min).

Although the invention has been described in terms of particular embodiments and applications, one of ordinary skill in the art, in light of this teaching, can generate additional embodiments and modifications without departing from the spirit of or exceeding the scope of the claimed invention. It should be emphasized that the above-described embodiments of the present invention, particularly any "preferred" embodiments, are merely possible examples of the invention of implementations, merely set forth for a clear understanding of the principles of the invention. Accordingly, it is to be understood that the drawings and descriptions herein are proffered by way of example to facilitate comprehension of the invention and should not be construed to limit the scope thereof.

We claim:
1. A process for preparing ziprasidone of formula I,

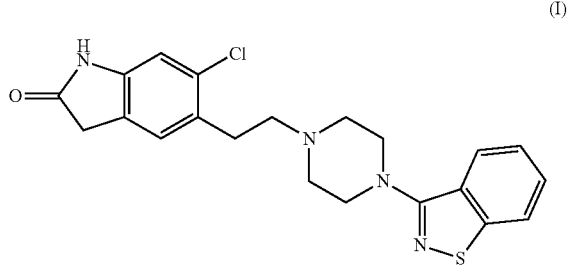 [SMILES: O=C1Cc2cc(CCN3CCN(c4nsc5ccccc45)CC3)c(Cl)cc2N1]

or a pharmaceutically acceptable salt or a solvate or a hydrate thereof;
comprising the steps of reacting 1-(1,2-benzisothiazol-3-yl)piperazine of formula II or its salt:

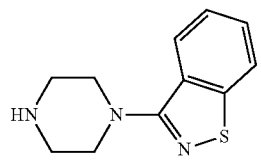

with 5-(2-haloethyl)-6-chloro-oxindole of formula III:

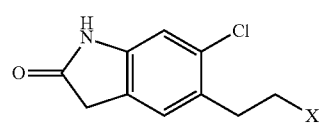

wherein X is a leaving group selected from fluoro, chloro, bromo, iodo or sulphonyl leaving group; in the presence of a dispersing agent and a base in a solvent to form ziprasidone of formula I; and optionally converting the ziprasidone formed into a pharmaceutically acceptable acid addition salts of ziprasidone; or a solvate or a hydrate thereof.

2. The process according to claim 1, wherein the dispersing agent is selected from the group consisting of modified sodium lignosulfonates kraft sodium lignosulfonates; naphthalene-formaldehyde condensates; naphthalenesulfonic acid formaldehyde condensate, or mixtures thereof.

3. The process according to claim 2, wherein the dispersing agent is naphthalene sulfonic acid formaldehyde.

4. The process according to claim 1, wherein the base is selected from alkali metal salt, hydroxides, organic tertiary bases or mixtures thereof.

5. The process according to claim 1, wherein the base is selected from sodium carbonate or bicarbonate or mixtures thereof.

6. The process according to claim 1, wherein the solvent is selected from the group consisting of substituted, unsubstituted, cyclic, bicyclic, saturated, or unsaturated, straight or branched hydrocarbon but not limited to aliphatic or aromatic hydrocarbon, having $C_6$-$C_{10}$ atoms, water, alcohols, ketones, esters, ethers and chlorinated solvents, or mixtures thereof.

7. The process according to claim 6, wherein the solvent is selected from the group consisting of toluene; ethyl acetate, propyl acetate, isopropyl acetate, butyl acetate and isobutyl acetate; water; methanol, ethanol and isopropanol; acetone, methyl ethyl ketone, methyl isobutyl ketone and diethyl ketone; tetrahydrofuran and dioxane; and methylene chloride, chloroform, carbontetrachloride and ethylene dichloride; or mixtures thereof.

8. The process according to claim 7, wherein the solvent is selected from the group consisting of alcohols and water or mixtures thereof.

9. The process according to claim 1, wherein the prepared ziprasidone or pharmaceutically acceptable salt or a solvate or a hydrate thereof has a purity of at least 98%.

* * * * *